(12) United States Patent
Aicher (10) Patent No.: US 7,191,670 B2
(45) Date of Patent: Mar. 20, 2007

(54) AUTOMATIC MICROBIAL AIR SAMPLING SYSTEM AND METHOD

(75) Inventor: Alan H. Aicher, Bristol, WI (US)

(73) Assignee: Hospira. Inc., Lake Forest, IL (US)

( * ) Notice: Subject to any disclaimer, the term of this patent is extended or adjusted under 35 U.S.C. 154(b) by 0 days.

(21) Appl. No.: 11/190,776

(22) Filed: Jul. 27, 2005

(65) Prior Publication Data

US 2005/0260765 A1 Nov. 24, 2005

Related U.S. Application Data

(62) Division of application No. 10/406,344, filed on Apr. 3, 2003, now Pat. No. 6,958,234.

(51) Int. Cl.
- *G01N 1/22* (2006.01)
- *G01N 1/28* (2006.01)
- *G01N 35/00* (2006.01)
- *C12Q 1/24* (2006.01)

(52) U.S. Cl. .......................... 73/863; 436/176; 436/181; 435/30; 422/4

(58) Field of Classification Search .................. 73/863; 436/176, 181; 422/4, 40; 435/30
See application file for complete search history.

(56) References Cited

U.S. PATENT DOCUMENTS

| | | | |
|---|---|---|---|
| 4,170,861 A | 10/1979 | Snyder et al. ................ 53/468 |
| 4,568,520 A * | 2/1986 | Ackermann et al. .......... 422/66 |
| 5,282,978 A | 2/1994 | Polk et al. ................ 422/63 X |
| 5,741,708 A | 4/1998 | Carey et al. .............. 422/63 X |
| 6,023,982 A | 2/2000 | Basch et al. ............. 73/863.25 |
| 6,138,521 A | 10/2000 | Basch et al. ............. 73/863.25 |
| 6,251,659 B1 | 6/2001 | Fukuzuno et al. ...... 435/287.3 X |

(Continued)

FOREIGN PATENT DOCUMENTS

DE 4032048 A * 4/1992

(Continued)

OTHER PUBLICATIONS

O. Pahl et al., "Comparison of Commonly Used Samplers With A Novel Bioaerosol Sampler With Automatic Plate Exchange", J. Aerosol Science, vol. 28, No. 3, pp. 427-435, 1997, month not given.

(Continued)

*Primary Examiner*—Thomas P. Noland
(74) *Attorney, Agent, or Firm*—Michael R. Crabb (57) ABSTRACT

A method and system for automated remote microbial air sampling includes a sampling enclosure positioned outside an isolator. An infeed sample receiver passes sample containers into the enclosure. An atrium is located within the enclosure and exposes containers to a gas sample. A remote sampling device collects the gas sample from the isolator and passes it to the atrium. A load arm is located within the enclosure. The load arm intermittently permits containers to enter the enclosure and moves containers to the atrium. An outfeed sample receiver passes containers out of the enclosure. The system allows addition and removal of containers from the air sampling system without interrupting the processing of the containers within the enclosure, and allows the first container supplied to the air sampling system to be the first exposed container removed therefrom.

2 Claims, 8 Drawing Sheets

U.S. PATENT DOCUMENTS

| | | |
|---|---|---|
| 6,321,609 B1 | 11/2001 | Mengel et al. ............ 73/863.21 |
| 6,335,166 B1 | 1/2002 | Ammann et al. ............... 435/6 |
| 6,470,760 B2 * | 10/2002 | Shinozaki et al. ....... 436/181 X |
| 6,706,519 B1 | 3/2004 | Kellogg et al. ....... 435/287.3 X |
| 2002/0132286 A1 | 9/2002 | Downs ................. 435/287.3 X |
| 2003/0170902 A1 * | 9/2003 | Heggs et al. ............ 436/181 X |
| 2004/0005714 A1 | 1/2004 | Safar et al. ................ 422/63 X |
| 2004/0185521 A1 | 9/2004 | Yoshida et al. ....... 435/309.1 X |

FOREIGN PATENT DOCUMENTS

| | | |
|---|---|---|
| DE | 195 03 663 C2 | 12/1996 |
| GB | 2247076 A * | 2/1992 |
| JP | 7-75551 | 3/1995 |
| JP | 2000157257 | 6/2000 |
| JP | 2000292325 | 10/2000 |

OTHER PUBLICATIONS

Tradeshow Flier, ""PasepT" Automated Isolator Environmental Monitoring", by Shibuya Kogyo Co., Ltd, Nov. 7, 2004, Pack Expo International 2004, Chicago, Illinois U.S.A.

* cited by examiner

AUTOMATIC MICROBIAL AIR SAMPLING SYSTEM AND METHOD

CROSS REFERENCE TO RELATED APPLICATION

This application is a divisional of U.S. Ser. No. 10/406,344 filed Apr. 3, 2003, now U.S. Pat. No. 6,958,234.

BACKGROUND OF THE INVENTION

The present invention relates to the field of air sampling systems, and more particularly to an automatic air sampling system that is useful for remotely sampling air from an isolated container-filling machine to assess the possibility of microbial contamination.

Isolated filling machines (isolators) are used in the pharmaceutical industry for sterile automated filling of pharmaceutical containers. Due to the sterility requirements of the isolator, objects passing into and out of the isolator must go through a cumbersome sterile "rapid" transfer port (RTP). This conventional sterile port arrangement greatly complicates the process of handling air monitoring equipment and materials that are required to determine air quality within the isolator.

Isolator space is very limited primarily because the only easy access is through fixed glove ports that have predetermined locations and limited reach. These glove ports have been provided so that an operator is able to perform routine clean up and sanitization between lots without opening the isolator and breaking its sterility. The arm length gloves are permanently installed in the isolator housing. Since operators have only limited movement and reach, many isolators have been designed in a "balcony" layout with nearly no horizontal flat surfaces inside the sterile manufacturing space. Accordingly, there is little space available for air monitoring equipment within the isolator.

Currently to test for microbial contamination, a technician must manually pass an agar filled Petri dish or settling jar into an isolator through the sterile transfer ports. The technician then opens the dish through the gloved ports and times its exposure within the isolator. The technician then covers the dish through the gloved ports, removes it from the isolator through the sterile transfer ports and transports the dish to an incubator for growth promotion. This cumbersome task may be performed repeatedly thought each day. When it is performed, great care must be taken to avoid disturbing the normal airflow patterns inside the isolator if representative results are to be expected.

Since operators are required to place their hands into close proximity with moving machinery, access to most of the glove ports is limited to times when the filling equipment inside the isolator is not running. Thus, the filling machine must be shut down during this activity for the safety of the technician. Further, the introduction of a growth media into the sterile isolator is problematic, since the growth media could be spilled within the isolator and contribute to the growth of undesired contaminants. The growth media can also come in contact with the gloves and be transferred to other areas of the isolator as the gloves are used to make normal adjustments and perform other tasks.

Therefore, a principal object of this invention is to provide a convenient method and means for collecting a gas sample from within an isolator, then remotely and automatically exposing it to media in a sample container outside the isolator so as to test the gas sample for microbial growth.

Another object of the invention is to provide a highly automated method and means for exposing media in sample containers to the gas sample such that fresh sample containers can be supplied and exposed sample containers can be removed without interrupting ongoing exposure of sample containers.

A further objective of the present invention is to provide a method and means designed for long periods of "unattended operation", and which requires only periodic maintenance to program cycles on the controller and to supply fresh sample containers and pick up the exposed containers.

A further object of the invention is to provide a highly automated method and means for processing sample containers wherein the first fresh container supplied is the first exposed container removed for testing.

An additional object of the invention is to provide a convenient platform for particulate monitoring, and for monitoring for concentrations of flammable or explosive gases, in the isolator as a part of the system.

These and other objects will be apparent to those skilled in the art.

SUMMARY OF THE INVENTION

The present invention relates to the field of air sampling systems, and more particularly to an automatic air sampling system that is useful for remotely sampling air from an isolated container-filling machine to assess the possibility of microbial contamination.

A method and system for automated remote microbial air sampling includes an enclosure positioned outside an isolator. The isolator typically encloses an aseptic filling machine or other process equipment that requires especially clean or sterile conditions inside the isolator. An infeed sample receiver passes gel media-containing sample containers into the enclosure. An atrium is located within the enclosure and exposes containers to a gas sample. A remote sampling device receives the gas sample from the isolator and passes it to the atrium. A load arm is located within the enclosure and intermittently permits containers to enter the enclosure and moves containers to the atrium. An outfeed sample receiver passes containers out of the enclosure. A user can utilize the infeed and outfeed sample receivers to supply and remove containers from the air sampling system without interrupting the processing of the container within the enclosure. The system is designed to allow the first container supplied to the air sampling system to be the first exposed container removed from the air sampling system. A continuous airflow is drawn through a sampling tube when the sample containers are being exposed, and even when there is no sample container in the atrium.

DESCRIPTION OF THE DRAWINGS

FIGS. 7A to 7M are sequential partial sectional top views of the device of this invention illustrating the motions resulting from the timing chart of FIG. 6.

DESCRIPTION OF THE PREFERRED EMBODIMENT

Figure 1:
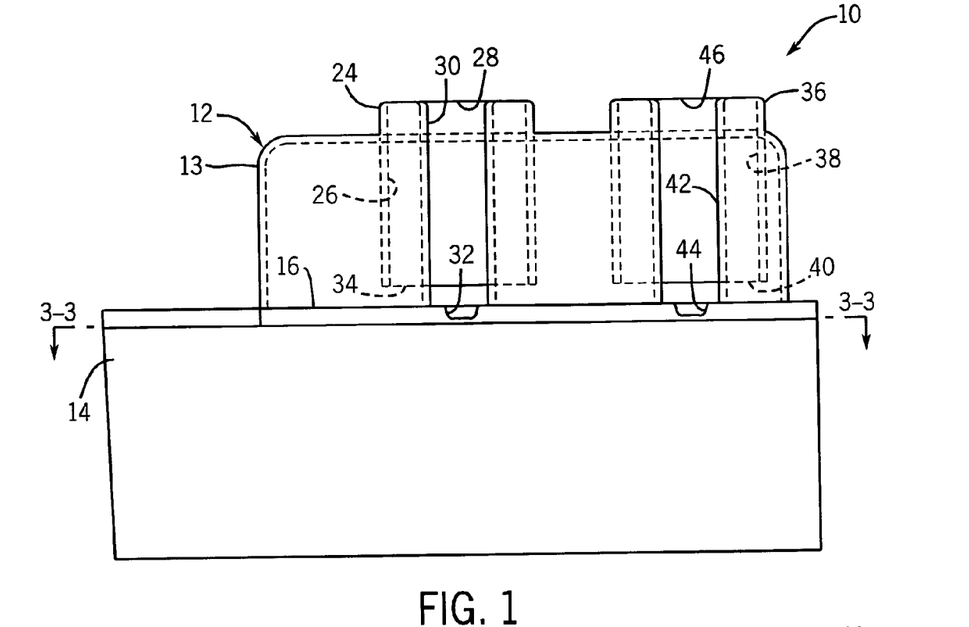
FIG. 1 is a side view of the device of this invention.
Figure 2:
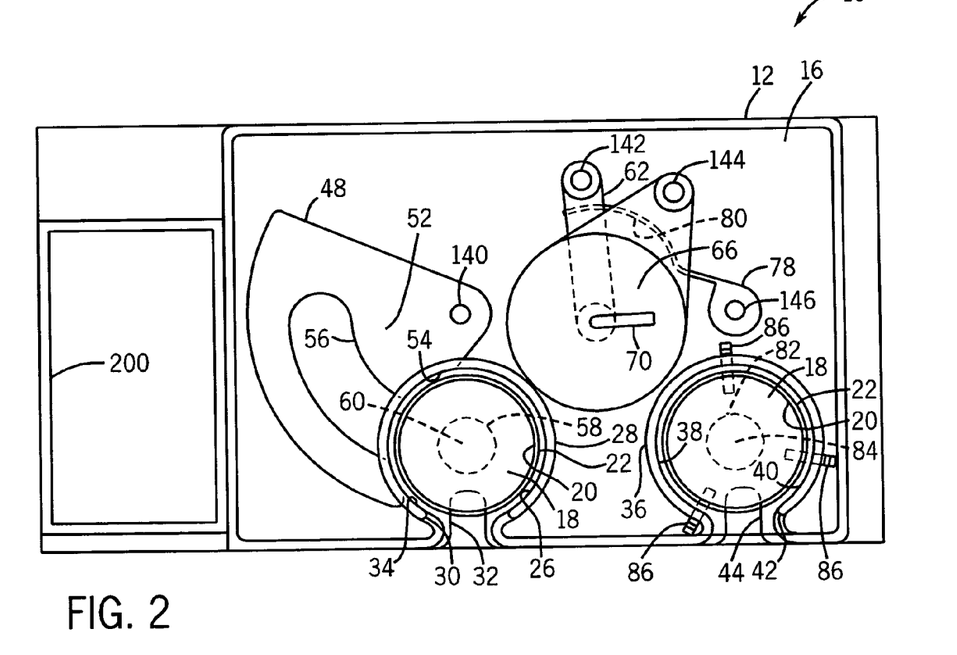
FIG. 2 is a top view of the device of this invention.

With reference to FIGS. 1 and 2, an air sampling system 10 includes an enclosure 12 for sampling and sample container transfer, which is defined between a cover 13 and a main housing 14 along a work surface 16 therebetween. The air sampling system 10 is designed to transfer and expose sample containers 18, including but not limited to an impermeable Petri dish or agar plate containing a gelatin growth media, to a gas sample. Once exposed, the sample containers 18 may be removed from the system, incubated for a time, and then evaluated to determine the microbial air quality of the gas sample. Typically, the sample containers 18 include a base portion 20 (containing the growth media) and a slidably removable lid portion 22.

An infeed sample container receiver 24 is associated with the sampling enclosure 12 and stores fresh sample containers 18 to feed into the enclosure 12 and transfer to an atrium 66. Although other forms, locations, and configurations are possible, the infeed sample container receiver 24 has no moving parts and is attached to or formed integral with the enclosure 12 (and more particularly with the cover 13) in the preferred embodiment. The infeed sample container receiver 24 is designed to receive additional sample containers 18 without interrupting the processing of the sample containers 18 within the enclosure 12 or the atrium 66.

The infeed sample container receiver 24 has a hollow tube or column portion 26 oriented in the vertical direction for storing the sample containers 18. An inlet opening 28 defines the top of the column portion 26 and receives fresh sample containers 18 into the column portion 26. A slot or side opening 30 is positioned along a length of the column portion 26 and provides hand access to the sample containers 18 located within the column portion 26. The side opening 30 may extend into the work surface 16 to provide an optional digit opening 32 which allows hand access beneath a sample container 18 that has passed into the enclosure 12. An outlet opening 34 defines the bottom of the column portion 26 and is associated with the enclosure 12 for passing the sample containers 18 from the infeed sample container receiver 24 to the atrium 66.

Thus, the sample containers 18 are supplied into the enclosure 12 via gravity. However, it will be understood by those skilled in the art, that while the present invention is described herein as using gravity to position the sample containers 18 within the air sampling system 10, one or more biasing mechanisms may be provided to achieve the same results without departing from the present invention.

An outfeed sample container receiver 36 is associated with the enclosure 12 and stores exposed sample containers 18 removed from the enclosure 12. Although other forms, locations, and configurations are possible, the outfeed sample container receiver 36 has no moving parts and is attached to or formed integral with the enclosure 12 (and more particularly with the cover 13). The outfeed sample container receiver 36 is designed to receive additional sample containers 18 and to have those sample containers 18 removed from the outfeed sample container receiver 36 without interrupting the processing of the sample containers 18 within the enclosure 12 or atrium 66. Further, the infeed sample container receiver 24 and the outfeed sample container receiver 36 are designed so that the first sample container 18 supplied to infeed sample container receiver 24 is the first exposed sample container 18 removed from the outfeed sample container receiver 36.

The outfeed sample container receiver 36 has a hollow column portion 38 oriented in the vertical direction for storing the exposed sample containers 18. An inlet opening 40 defines the bottom of the column portion 38 and is associated with the enclosure 12 for passing the exposed sample containers 18 from the atrium 66 within the enclosure 12 to the outfeed sample container receiver 36. A slot or side opening 42 is positioned along a length of the column portion 38 which provides hand access to the sample containers 18 located within the column portion 38. The side opening 42 may extend into the work surface 16 to provide an optional digit opening 44 which allows hand access beneath a sample container 18 that has not yet passed into the column portion 38. An outlet opening 46 defines the top of the column portion 38 and allows removal of the exposed sample containers 18 from the column portion 38.

Figure 3:
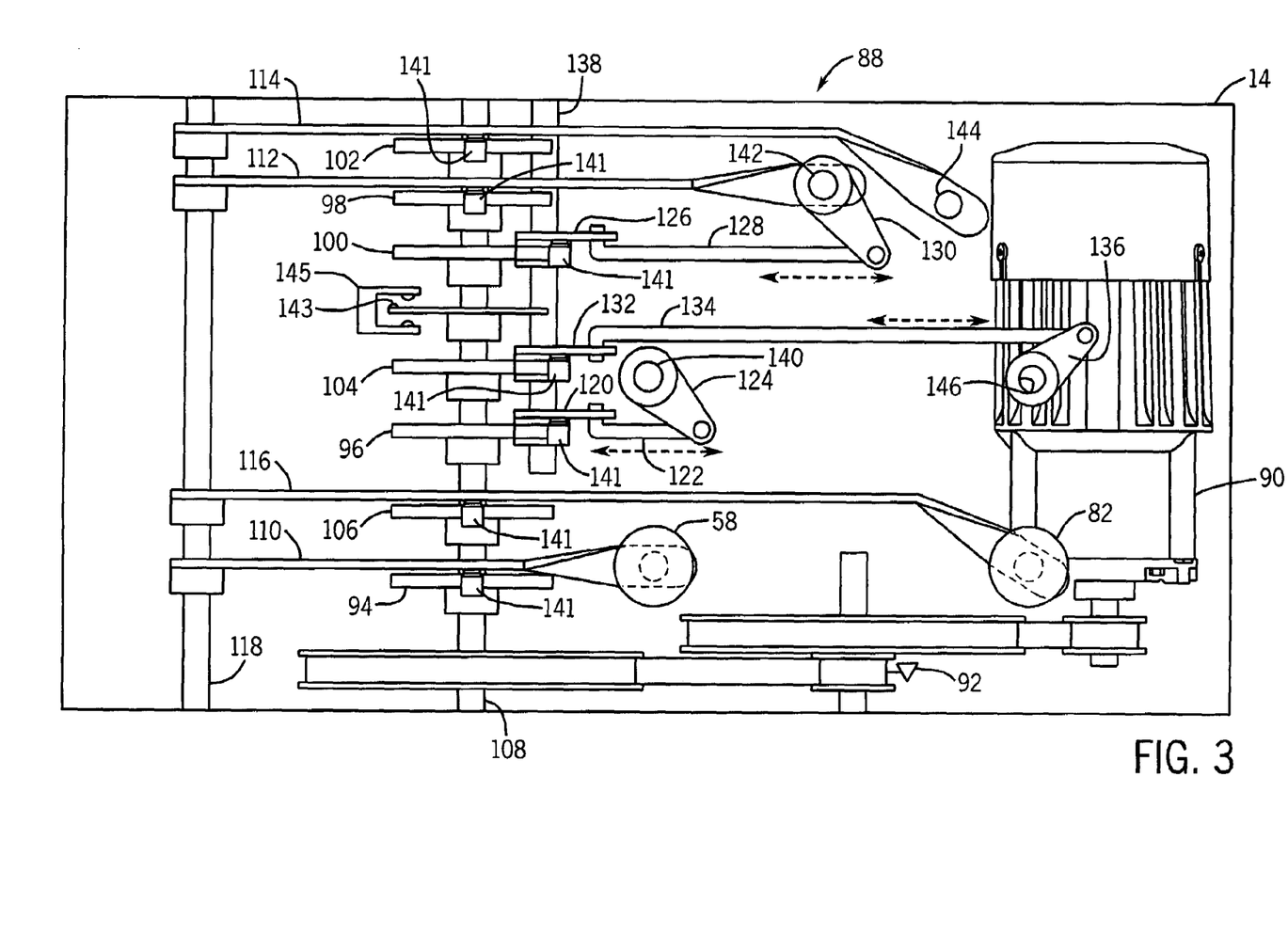
FIG. 3 is a top view of the device of this invention taken on line 3—3 of FIG. 1.
Figure 6:
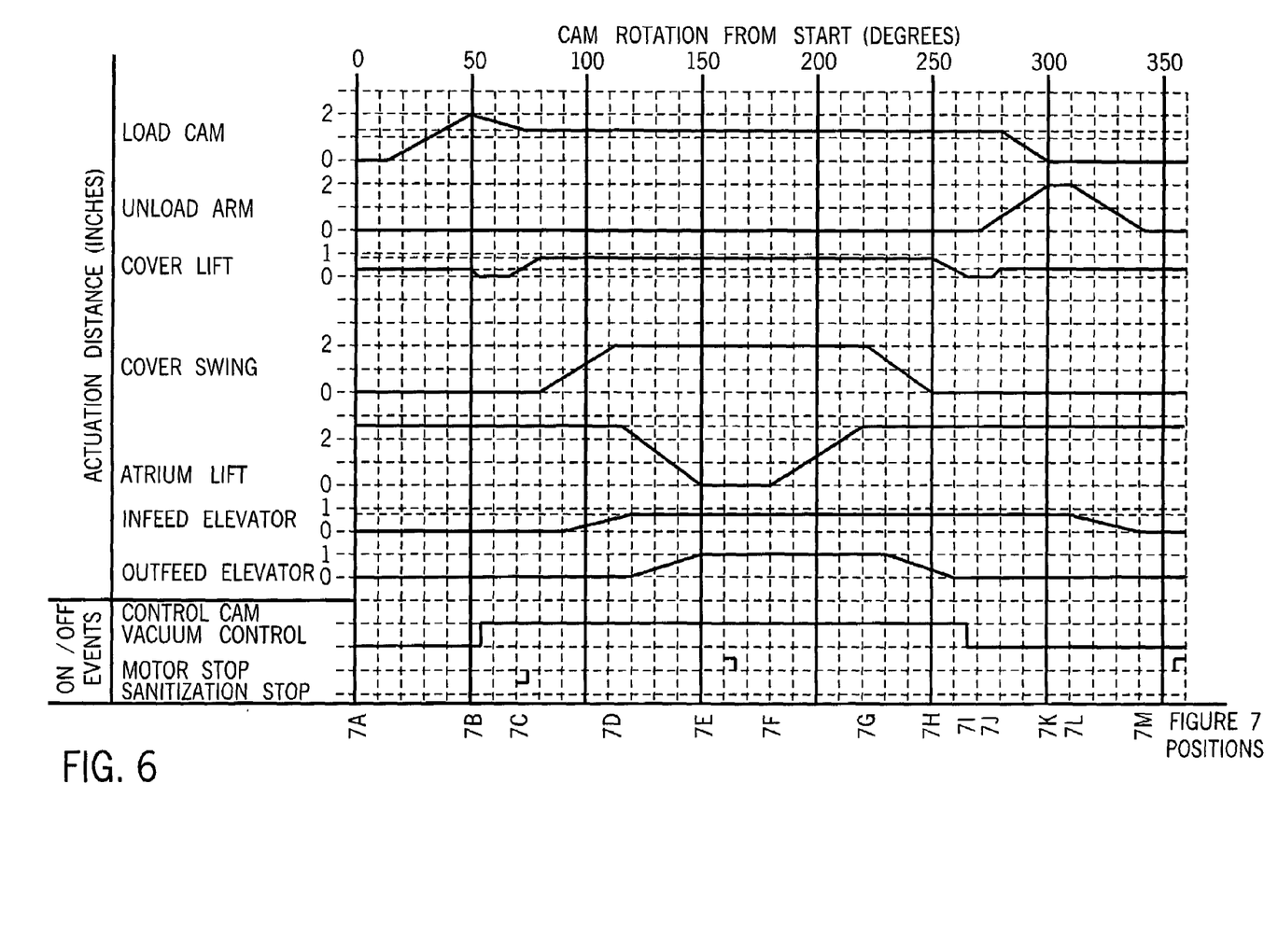
FIG. 6 is a timing chart detailing the movement of portions of the device of this invention.

FIGS. 7A to 7M show the sequential positions of the moving components of the air sampling system 10 housed in enclosure 12 as the insertion, exposure, and removal of sample containers 18 takes place. It should be noted that the components do not all function in the same plane at the same time; for some of the components move in a direction perpendicular to the work surface 16. These sequential positions are shown graphically in the timing chart of FIG. 6. From the timing chart of FIG. 6, one skilled in the mechanical arts can develop an appropriate cam system 88, as shown in FIG. 3, with appropriate profiles or configurations of the cams, followers, shafts, and arms shown to achieve the desired movements of the components and containers during the sampling cycle.

With reference to FIGS. 2 and 7A–7M, a load arm 48 is located within the enclosure 12 and adjacent to the inlet opening 28 of the infeed sample container receiver 24. The load arm 48 both restricts the passage of fresh sample containers 18 into the enclosure 12 and moves sample containers 18 within the enclosure 12 from beneath the inlet opening 28 to a sampling or exposure position 50 inside the atrium 66.

Figure 7A:
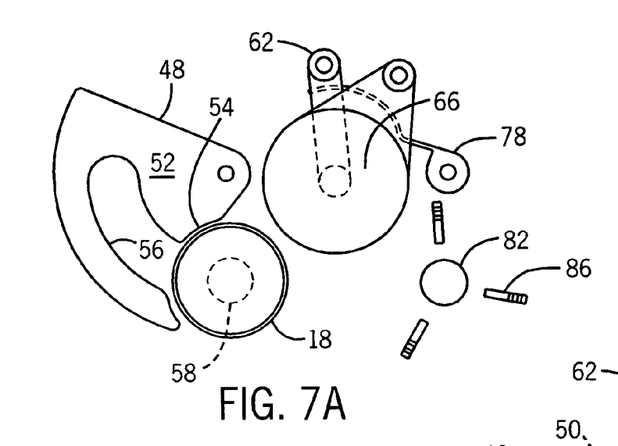
Figure 7B:
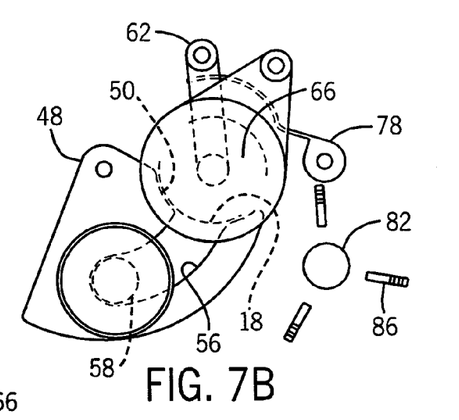
Figure 7C:
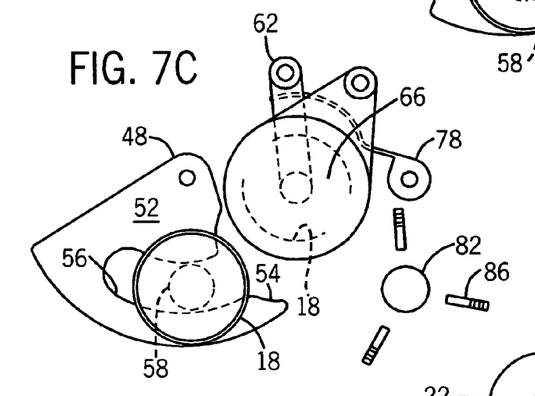

A forward surface 54 on the load arm moves a sample container from beneath the inlet opening 28 to the sampling or exposure position 50 when the load arm 48 is extended (FIG. 7B). The load arm 48 has a sample retention surface 52 which supports the next sample container 18 in the sample container receiver 24 as the load arm 48 moves from the position in FIG. 7A to the position in FIG. 7B and back to the position in FIG. 7C. This prevents a sample container 18 from exiting the inlet opening 28 when the load arm 48 is in an extended position (FIG. 7B) or in a mid position between the retracted and extended positions (FIG. 7C). The load arm 48 has an elevator slot 56 for permitting the load arm to pass about an infeed elevator 58 while the infeed elevator 58 is extended (FIGS. 7D–7K).

Figure 7D:
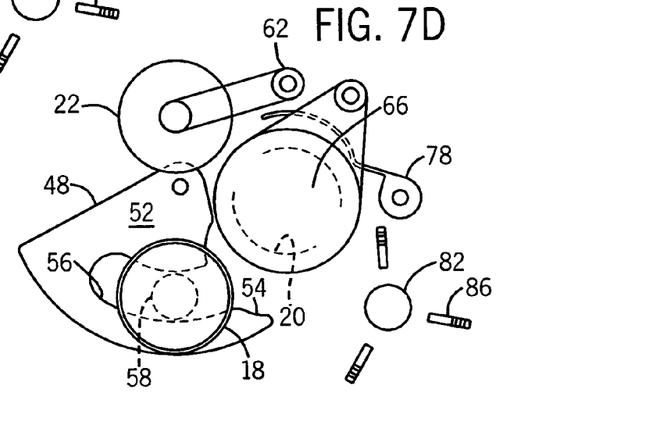
Figures 7E, 7F, 7G, 7H:
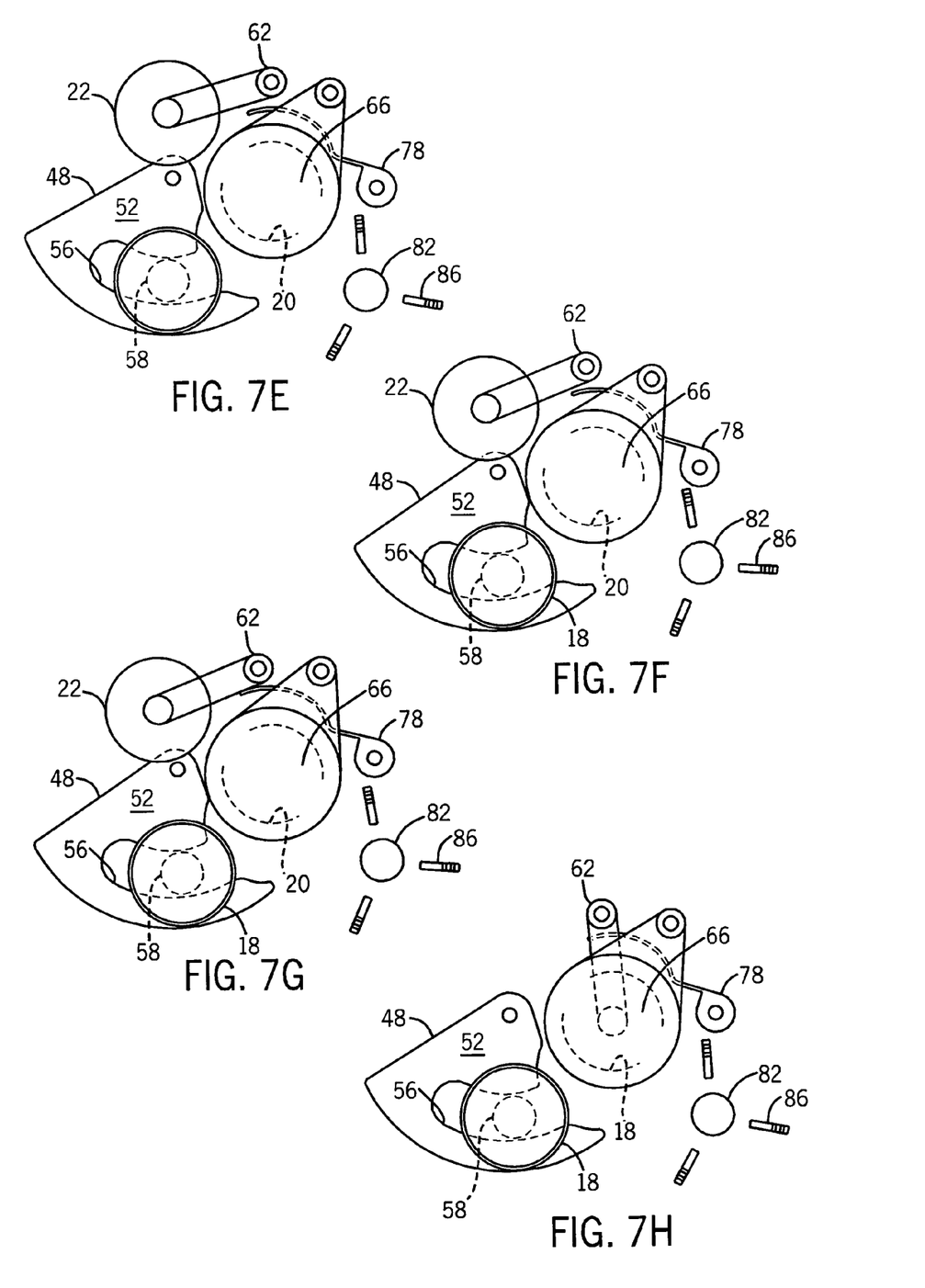
Figures 7I, 7J, 7K, 7L, 7M:
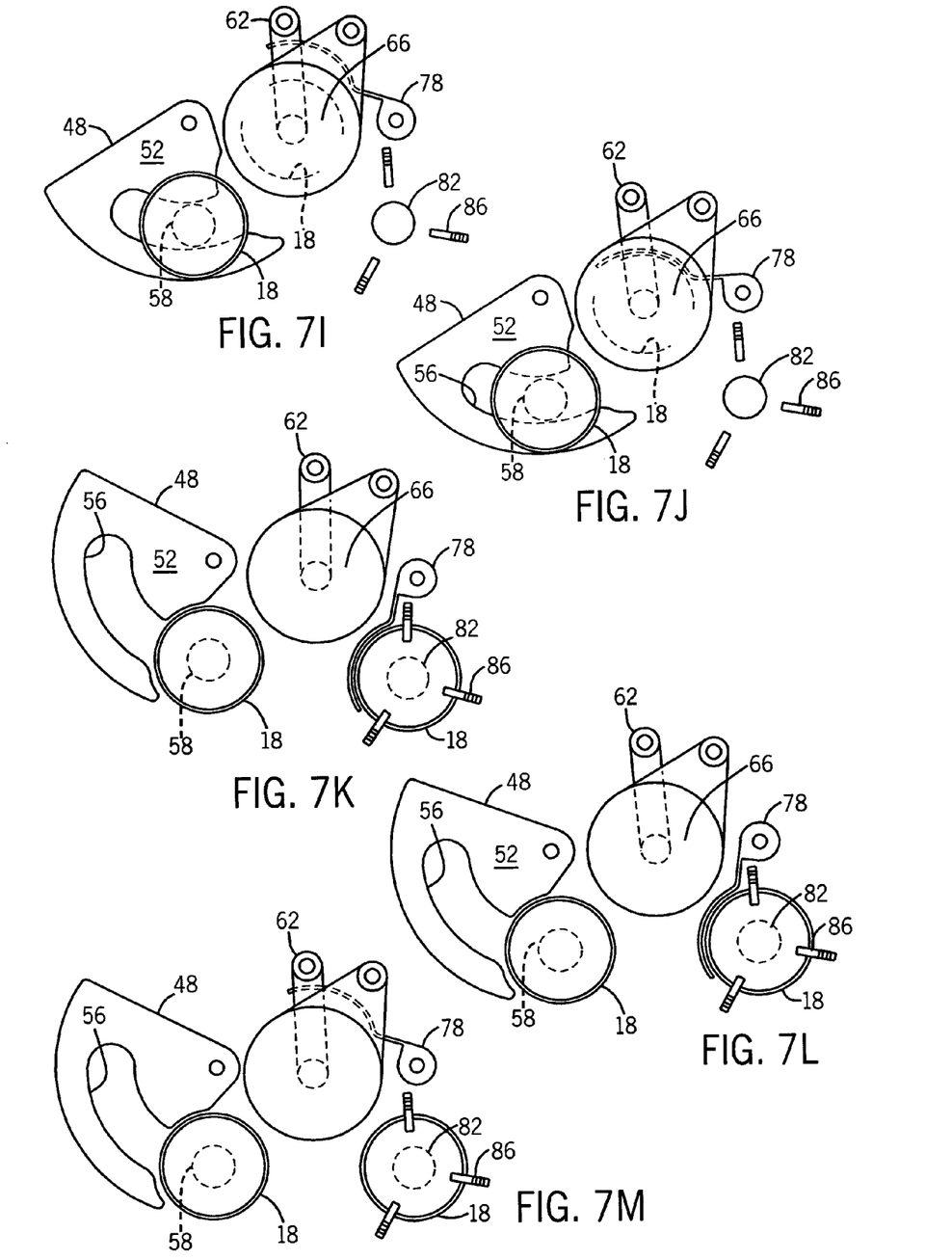

With reference to FIGS. 2, 4 and 7A–7M, the infeed elevator 58 is positioned beneath the inlet opening 28 of the infeed sample container receiver 24. The infeed elevator 58 has an end portion 60 that is movable (i.e., can be raised and lowered) with respect to the work surface 16 so as to be flush with the work surface 16 when in a retracted position (FIGS. 7A–7C and 7M). The end portion 60 extends upwardly (FIG. 4) to engage the lowermost sample container 18 in the infeed sample container receiver 24 when the load arm 48 is in a mid position (FIG. 7D) thus lifting the lowermost sample container 18, and those above, from the sample retention surface 52. The end portion 60 lowers the lowermost sample container 18, and those above, to the work surface 16 when the load arm 48 has moved to the retracted position (FIGS. 7L–7M).

With reference to FIGS. 2, 4, and 7A–7M, a cover arm 62 is positioned adjacent to the sampling or exposure position 50 and has a suction element 64 that removably fastens to the lid portion 22 of the sample container 18 (FIG. 7C). Once fastened to the lid portion 22 the cover arm 62 raises and rotates, lifting the lid portion 22 and opening the base portion 20 (FIG. 7D). This allows the media in the base portion 20 to be exposed to a gas sample. Once the exposure for the desired time is completed, the cover arm 62 rotates and lowers; the suction element 64 then releases the lid portion 22, thus replacing the lid portion 22 and closing the base portion 20 of the sample container 18 (FIGS. 7G–7J).

With reference to FIGS. 2, 7A–7M and 5, an atrium 66 is positioned adjacent to the sampling or exposure position 50 and the cover arm 62. The atrium 66 exposes media in the base portion 20 to a gas sample. The atrium 66 has a cover 68 with an inlet 70 for gas samples and a contoured surface 72 to evenly distribute the gas sample over the growth media contained in the base portion 20. The cover 68 is vertically displaceable, lowering and raising respectively to cover and uncover the base portion 20 at the beginning and the end of the exposure period (FIGS. 7D–7G). The atrium 66 also has a base 74 situated within work surface 16 with channels (not shown) for directing the flow of the gas sample out of the atrium 66 and an outlet 76 for removing the gas sample.

With reference to FIGS. 2 and 7A–7M, an unload arm 78 is located within the enclosure 12 and adjacent to the atrium 66. The unload arm 78 has a forward face 80 which engages the exposed sample container 18 when the unload arm 78 is rotated from a retracted position (FIG. 7I), to an intermediate position (FIG. 7J). Once engaged, the unload arm 78 rotates to an extended position (FIGS. 7K–7L), moving the exposed sample container 18 from the atrium 66 and adjacent to the inlet opening 40 of the outfeed sample container receiver 36.

With reference to FIGS. 1, 2, 4 and 7A–7M, an outfeed elevator 82 is positioned beneath the inlet opening 40 of the outfeed sample container receiver 36. The outfeed elevator 82 has an end portion 84 that is movable (i.e., can be raised and lowered) with respect to the work surface 16 so as to be flush with the work surface 16 when in a retracted position (FIGS. 7A–7D and 7I–7M). The end portion 84 engages the base portion 20 (FIG. 2) and extends upwardly (FIG. 4) to remove the exposed sample container 18 from the enclosure 12 and into the outfeed sample container receiver 36 (FIGS. 7E–7G) and then retracts to the work surface 16 (FIG. 7H).

Figure 4:
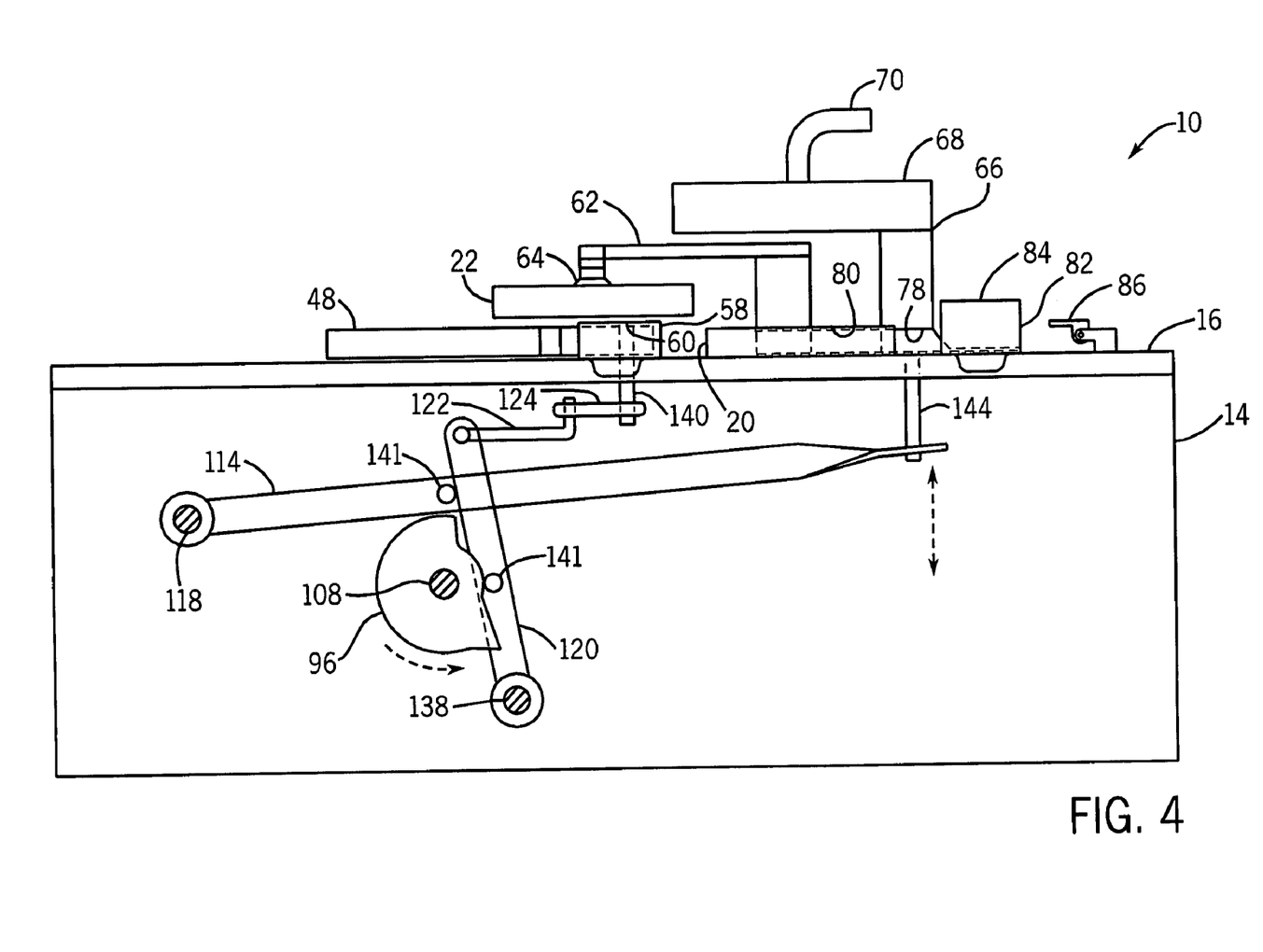
FIG. 4 is a partial sectional side view of the device of this invention.

As best seen in FIGS. 2 and 4, several latches 86 are arranged and positioned below or outside the inlet opening 40 of the outfeed sample container receiver 36. The latches 86 are repeatably upwardly deflectable to permit an exposed sample container 18 to displace the latches 86 and pass past the latches 86 into the outfeed sample container receiver 36 when the outfeed elevator 82 is in an extended position (FIG. 5, FIGS. 7E–7G). Once the exposed sample container 18 passes past the latches 86, the latches 86 return to a non-deflected position preventing the exposed sample container 18 in the outfeed sample container receiver 36 from passing back into the equipment cover 12. Optional biasing means such as springs (not shown) can be used to urge the latches 86 to their non-deflected positions.

With reference to FIGS. 2–5, the mechanical housing 14 contains a cam system 88 for timing and animating the various moving elements contained in the enclosure 12. The timing of the animation in the cam system 88 is controlled by the particular shape of each cam. Each vertical moving element contained in the equipment cover 12 has a lift arm associated between the vertical moving element and its respective cam. Each horizontal moving element contained in the enclosure 12 has a swing arm associated between the horizontal moving element and its respective cam.

The cam system 88 includes a motor 90 and belt system 92 for supplying mechanical energy to the cam system 88. Infeed elevator cam 94, load arm cam 96, cover lift cam 98, cover swing cam 100, atrium cam 102, unload arm cam 104, and outfeed elevator cam 106 are mounted on a rotatable cam drive shaft 108 which is animated by the motor 90 and belt system 92. Infeed lift arm 110, cover lift arm 112, atrium lift arm 114, and outfeed lift arm 116 are pivotally mounted on lift pivot shaft 118. Load swing arm 120 having extension member 122 and pivot arm 124, cover swing arm 126 having extension member 128 and pivot arm 130, and unload swing arm 132 having extension member 134 and pivot arm 136 are pivotally mounted on swing pivot shaft 138.

The load arm 48 is connected to the pivot arm 124 of the load swing arm 120 through rod 140. A cam follower 141 pivotally mounted on the load swing arm 120 rests against the load arm cam 96 so that as the motor 90 rotates the load arm cam 96 the load swing arm 120 acts on the rod 140 through the extension member 122 and pivot arm 124 to rotate the load arm 48.

The infeed elevator 58 rests on the infeed lift arm 110. A cam follower 141 pivotally mounted on the infeed lift arm 110 rests against the infeed elevator cam 94 so that as the motor 90 rotates the infeed elevator cam 94 the infeed lift arm 110 raises and lowers the infeed elevator 58.

The cover arm 62 rests on the cover lift arm 112 and is connected to the pivot arm 130 of the cover swing arm 126 through rod 142. A cam follower 141 pivotally mounted on the cover lift arm 112 rests against the cover swing cam 98 so that as the motor 90 rotates the cover swing cam 98 the cover lift arm 112 raises and lowers the cover arm 62 through rod 142. A cam follower 141 pivotally mounted on the cover swing arm 126 rests against the cover swing cam 100 so that as the motor 90 rotates the cover swing cam 100 the cover swing arm 126 acts on the rod 142 through the extension member 128 and pivot arm 130 to rotate the cover arm 62.

The atrium 66 is connected to rod 144 which rests on the atrium lift arm 114. A cam follower 141 pivotally mounted on the atrium lift arm 114 rests against the atrium cam 102 so that as the motor 90 rotates the atrium cam 102 the atrium lift arm 114 raises and lowers the atrium 66 through rod 144.

The unload arm 78 is connected to the pivot arm 136 of the unload swing arm 132 through rod 146. A cam follower 141 pivotally mounted on the unload swing arm 132 rests against the unload arm cam 104 so that as the motor 90 rotates the unload arm cam 104 the unload swing arm 132 acts on the rod 146 through the extension member 134 and pivot arm 136 to rotate the unload arm 78.

The outfeed elevator 82 rests on the outfeed lift arm 116. A cam follower 141 pivotally mounted on the outfeed lift arm 116 rests against the outfeed elevator cam 106 so that as the motor 90 rotates the outfeed elevator cam 106 the outfeed lift arm 116 raises and lowers the outfeed elevator 82.

Cam 143 in FIG. 3 provides timing signals to the process controller 200 via a sensor array 145. Preferably the cam 143 has a plurality of notches, grooves or holes therein and the sensor array 145 is a photoelectric eye array. The timing signals indicate specific positions of the cam shaft that are necessary to control the process. These signals are used to stop the motor 90, and control the vacuum lift vacuum valve 174 (FIG. 5) during the preprogrammed machine cycles.

Figure 5:
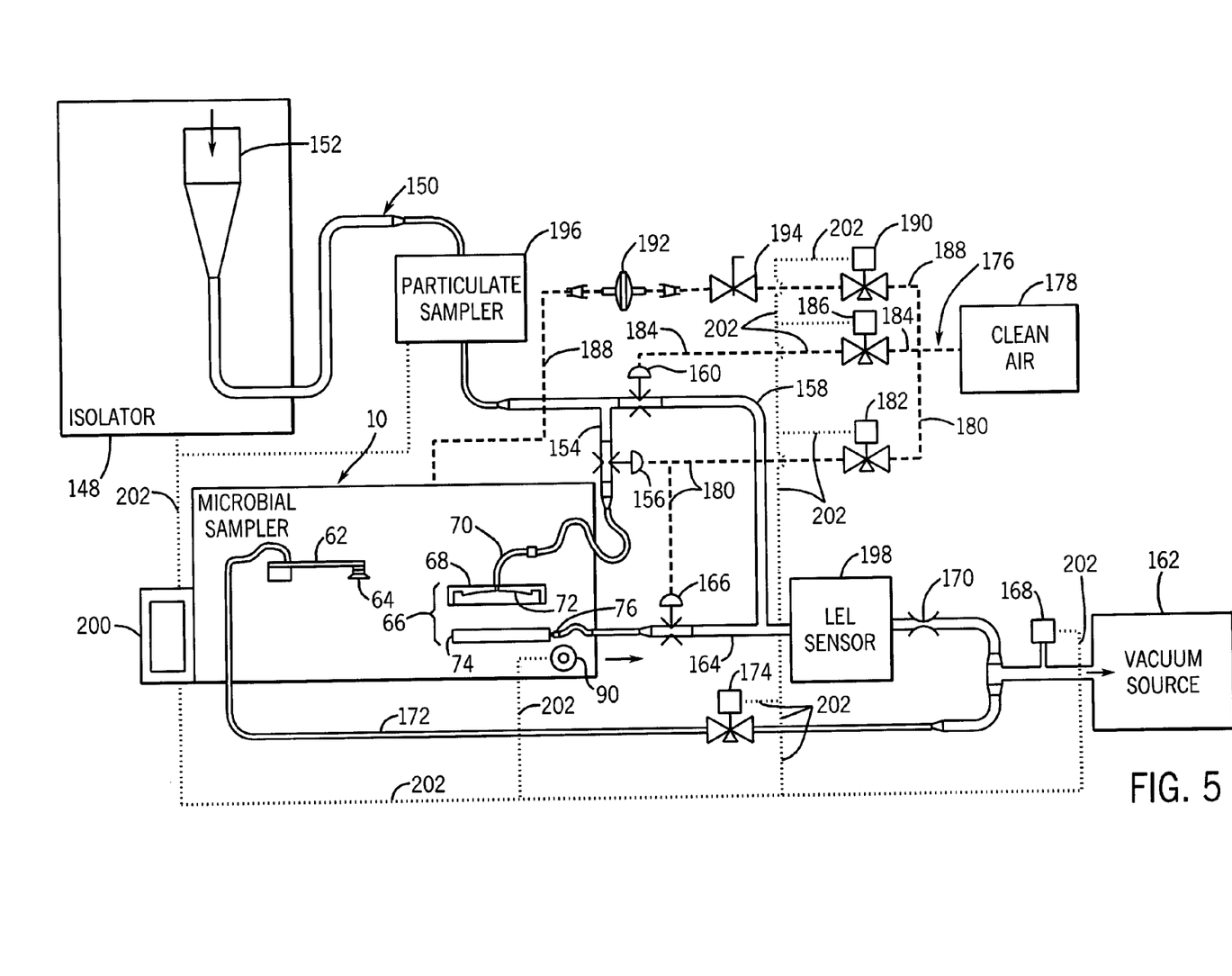
FIG. 5 is a schematic view of the device of this invention in use with an isolator and other devices.

With reference to FIG. 5, the air sampling system 10 is designed to function unattended for long periods of time as an automated remote microbial air sampling system to facilitate testing the air quality of an isolator 148 for microbial contamination. The air sampling system 10 includes a sample supply system 150 for obtaining a gas sample for the enclosure 12 positioned outside of the isolator 148. The sample supply system 150 includes a remote sampling device 152, such as an isokinetic sampling horn, connected in flow communication between the isolator 148 and the enclosure 12 to deliver the gas sample from the isolator 148 to the atrium 66 without significantly disrupting the flow of air within the isolator.

The sample supply system 150 includes an atrium conduit 154, with a valve 156, connecting the remote sampling device 152 to the inlet 70 of the atrium 66. The valve 156 is a pinch valve that controls the flow of gas thorough the conduit 154.

A bypass conduit 158, with a valve 160, connects the atrium conduit 154, upstream of the atrium 66, to a vacuum source 162. The bypass conduit 158 allows gas sample from the remote sampling device 152 to bypass the atrium 66 when there is no sample container 18 to be exposed. The valve 160 is a pinch valve that controls the flow of gas thorough the conduit 158.

An atrium outlet conduit 164, with a valve 166, connects the outlet 76 of the atrium 66 to the bypass conduit 158 and thus the vacuum source 162. The valve 166 is a pinch valve that controls the flow of gas thorough the conduit 164.

Accordingly, when valves 156 and 166 are open and valve 160 is closed, the vacuum source 162 pulls or draws a gas sample from the remote sampling device 152 and though the closed atrium 66. Conversely, when valves 156 and 166 are closed and valve 160 is open, the vacuum source 162 pulls a gas sample from the remote sampling device 152 and though the bypass conduit 158. Thus, the sample supply system 150 maintains a constant gas sample flow from the isolator 148, and an intermittent gas sample flow to the atrium 66.

A vacuum switch 168 and flow control orifice 170 are positioned upstream of the vacuum source 162 along the bypass conduit 158 for controlling the flow of gas to the vacuum source 162.

A cover suction conduit 172, having a valve 174, connects the suction element 64 of the cover arm 62 to the vacuum source 162. The valve 174 is a solenoid valve that controls the flow of gas thorough the conduit 172. The cover suction conduit 172 provides vacuum for removably engaging the suction element 64 to a lid portion 22 of a sample container 18.

The air sampling system 10 further includes a clean air supply system 176 having a clean air source 178 that supplies clean air to open and close pneumatic pinch valves 156, 160, and 166. A first conduit 180 connects the clean air source 178 to pneumatic pinch valves 156 and 166 to open and close these valves. The flow of air through the first conduit 180 is controlled by a solenoid valve 182 connected thereto. A second conduit 184 connects the clean air source 178 to pneumatic pinch valve 160 to open and close this valve. The flow of air through the second conduit 184 is controlled by a solenoid valve 186 connected thereto.

A third conduit 188 passes through a solenoid valve 190, a needle valve 194 and a microbially retentive air filter 192, and connects the clean air source 178 to the enclosure 12. The third conduit 188 provides positive pressure to the enclosure 12 to prevent outside contaminants from entering the enclosure 12. The solenoid valve 190 controls the flow of air through the third conduit 188 into the enclosure 12. The air filter 192 is a 0.2 micron filter which reduces the airborne contaminants that can pass from the clean air source 178 to the enclosure 12.

It will be understood by those skilled in the art that while the present invention is described herein as being isolated via positive air pressure within the enclosure 12, seals (not shown) may also be provided about the outlet opening 34 and inlet opening 40 to further isolate the enclosure 12.

The air sampling system 10 may further include a particulate sampler 196 connected in flow communication with the remote sampling device 152 upstream from the atrium 66. The particulate sampler 196 receives and analyzes the gas sample for particulate matter upstream from the atrium.

The air sampling system 10 may further include a lower explosive limit sensor (LEL) 198 connected in flow communication with the remote sampling device 152 downstream from the atrium 66. The LEL sensor 198 receives and analyzes the gas sample for explosive properties if necessary.

With reference to FIGS. 2 and 5, a process controller 200 is located above outside the enclosure 12 and flush with the work surface 16. The process controller 200 monitors and controls the entire air sampling system 10, including the motor 90, vacuum switch 168, and solenoid valves 174, 182, 186, and 190 via electronic signal line 202.

Further, the process controller 200 receives information from the isolator 148 via electronic signal line 202. Particularly the process controller 200 receives information regarding the timing of when the isolator 148 is to be routinely sanitized with a sterilizing gas. The enclosure 12 also needs to be routinely sanitized. Thus, the process controller 200 is programmed to pull the sterilizing gas from the isolator 148 and into the enclosure 12 via the open atrium 66 to sanitize the inside of the enclosure 12. During the sanitization, there are no sample containers 18 in the enclosure 12, the infeed sample container receiver 24, or in the outfeed sample container receiver 36; and the infeed and outfeed sample receivers 24 and 36 are closed with plugs (not shown) to seal the enclosure 12. The process controller 200 is a touch screen controller available from Z World Engineering of Davis, Calif., U.S.A. under the trade designation PK2600.

It is therefore seen that the present invention provides a convenient method and means for collecting a gas sample from within an isolator 148, then remotely and automatically exposing it to media in a sample container outside the isolator so as to test the gas sample for microbial growth. The present invention also provides a highly automated method and means for exposing media in sample containers 18 to a gas sample such that fresh sample containers can be supplied and exposed sample containers can be removed without interrupting ongoing exposure of sample containers. The present invention also provides a method and means capable of processing sample containers 18 wherein the first fresh container 18 supplied is the first exposed container 18 that can be removed for testing. The system is designed to run unattended for long periods of time, and requires only periodic maintenance to program cycles on the controller and to supply fresh sample containers and pick up the exposed containers.

It is therefore seen that this invention will accomplish at least all of its stated objectives.

I claim:

1. A method of exposing sample containers to a gas sample, comprising:

providing an air sampling system having a sampling enclosure and an atrium located within the sampling enclosure;

automatically passing a sample container into the sampling enclosure;

automatically exposing the sample container to a gas sample through the atrium;

automatically passing the exposed sample container out of the sampling enclosure and into an outfeed sample container receiver for holding exposed sample containers; and supplying sample containers to the air sampling system and removing exposed sample containers from the outfeed sample container receiver wherein the first container supplied to the air sampling system is the first exposed container removed from the outfeed sample container receiver even if additional exposed sample containers are passed into the outfeed sample container receiver while the first exposed container is in the outfeed sample container receiver.

2. A method of exposing sample containers to a gas sample, comprising:

providing an air sampling system having a sampling enclosure and an atrium located within the sampling enclosure;

automatically passing a sample container into the sampling enclosure;

automatically exposing the sample container to a gas sample through the atrium;

automatically passing the exposed sample container out of the sampling enclosure;

supplying sample containers to the air sampling system and removing exposed sample containers from the air sampling system wherein the first container supplied to the air sampling system is the first exposed container removed from the air sampling system; and maintaining the atmosphere inside the sample enclosure sterile via a continuous purge of microbially filtered air.

* * * * *